United States Patent [19]
Knollenberg et al.

[11] Patent Number: 5,459,569
[45] Date of Patent: Oct. 17, 1995

[54] NONINTRUSIVE MODULAR PARTICLE DETECTING DEVICE

[75] Inventors: Scott C. Knollenberg; Robert G. Knollenberg, both of Boulder, Colo.

[73] Assignee: Particle Measuring Systems, Inc., Boulder, Colo.

[21] Appl. No.: 51,055

[22] Filed: Apr. 21, 1993

[51] Int. Cl.$^6$ .......................... G01N 21/00; G01N 21/05
[52] U.S. Cl. .......................... 356/338; 356/339; 250/574
[58] Field of Search ................... 356/335–343, 356/36; 250/574, 573

[56] References Cited

U.S. PATENT DOCUMENTS

| Re. 33,213 | 5/1990 | Borden | 356/338 |
|---|---|---|---|
| 4,291,983 | 9/1981 | Kraft et al. | 356/338 |
| 4,571,079 | 2/1986 | Knollenberg | 356/336 |
| 4,673,820 | 6/1987 | Kamen | 250/573 |
| 4,798,465 | 1/1989 | Knollenberg | 356/336 |
| 4,885,473 | 12/1989 | Shotnes et al. | 250/574 |
| 5,033,852 | 7/1991 | Zaglio | 356/337 |

OTHER PUBLICATIONS

Knollenberg and Veal, Optical Partical Monitors, Counters and Spectrometers: Performance, Characterization, Comparison and Use; Procedings of the Institute of Environmental Sciences Conference, San Diego, California, 1991, pp. 751–771.

Primary Examiner—Vincent P. McGraw
Assistant Examiner—K. P. Hantis
Attorney, Agent, or Firm—Robert E. Harris

[57] ABSTRACT

A modular particle detecting device is disclosed for nonintrusive in-situ detection of particles passing through a sensing region. The device is particularly useful for microcontamination control in semiconductor processing environments, and includes, as separate components, a viewing unit and a sensing unit. The viewing unit has a detecting window and heated illuminating and discharge windows for condensation control. A fluid passage connectable to a flow line enables particle-carrying fluid to pass through a sensing region within the passage. The sensing unit has illuminating circuitry for providing light through the illuminating window to the sensing region, and has detecting circuitry to receive, through the detecting window, light scattered at the sensing region to thereby detect particles in fluid then at the sensing region without physical intrusion of the sensing unit into the sensing region. The sensing unit is mounted on the viewing unit when operationally positioned, and is readily removable to allow servicing and/or alternate use without interupting fluid flow through a flow line having the viewing unit connected therewith.

9 Claims, 3 Drawing Sheets

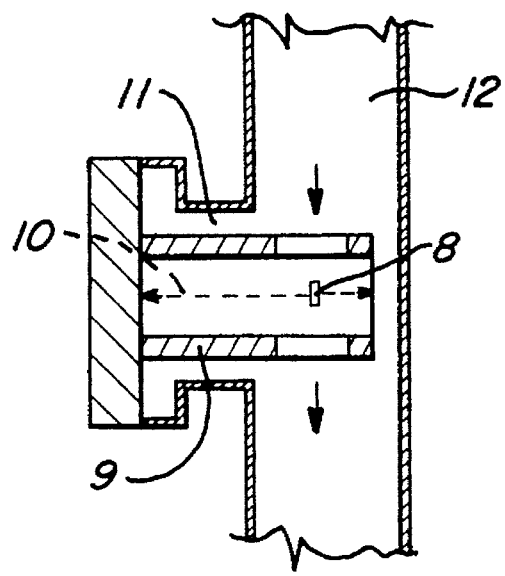
Fig_1
PRIOR ART
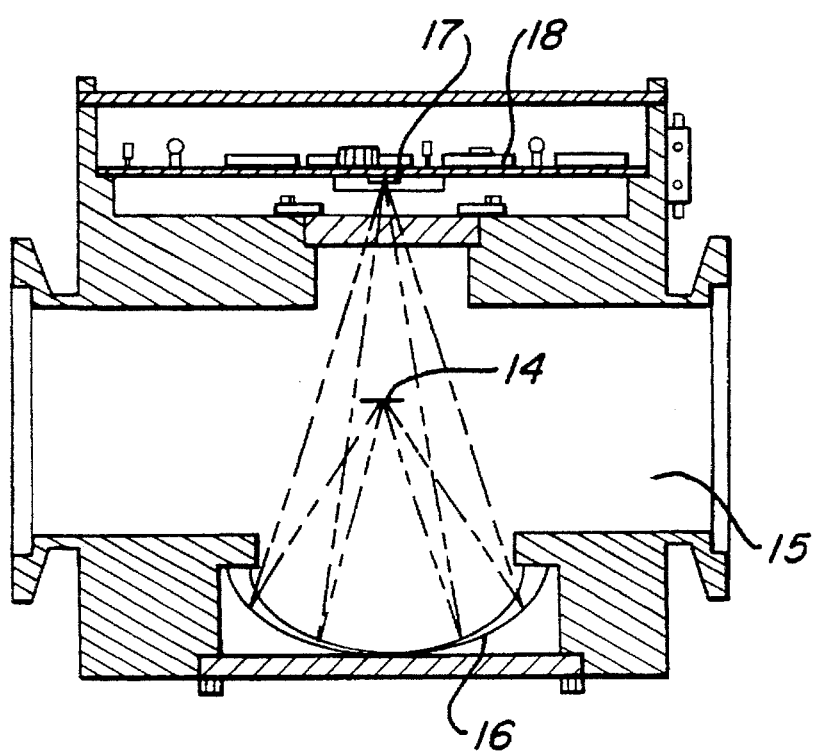
Fig_2
PRIOR ART

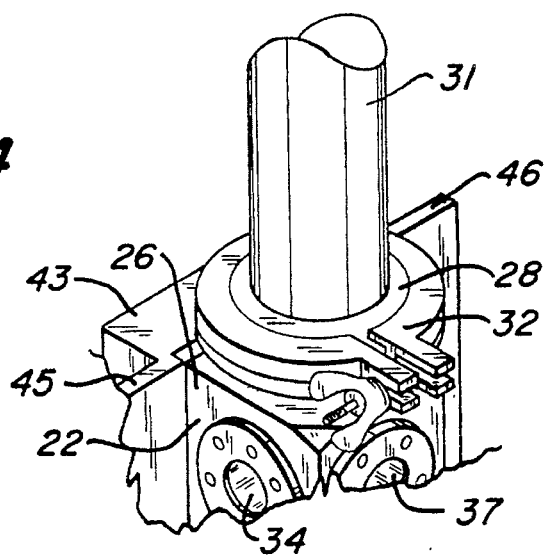
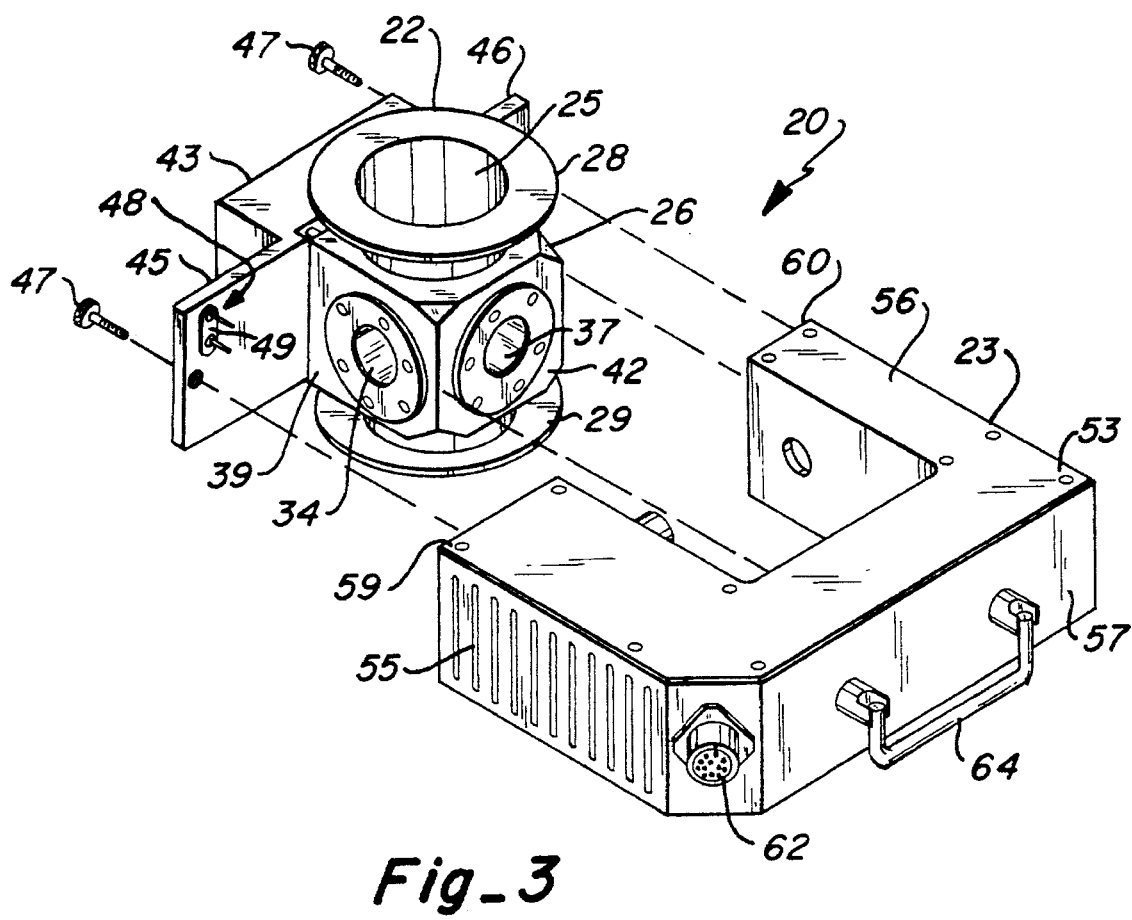

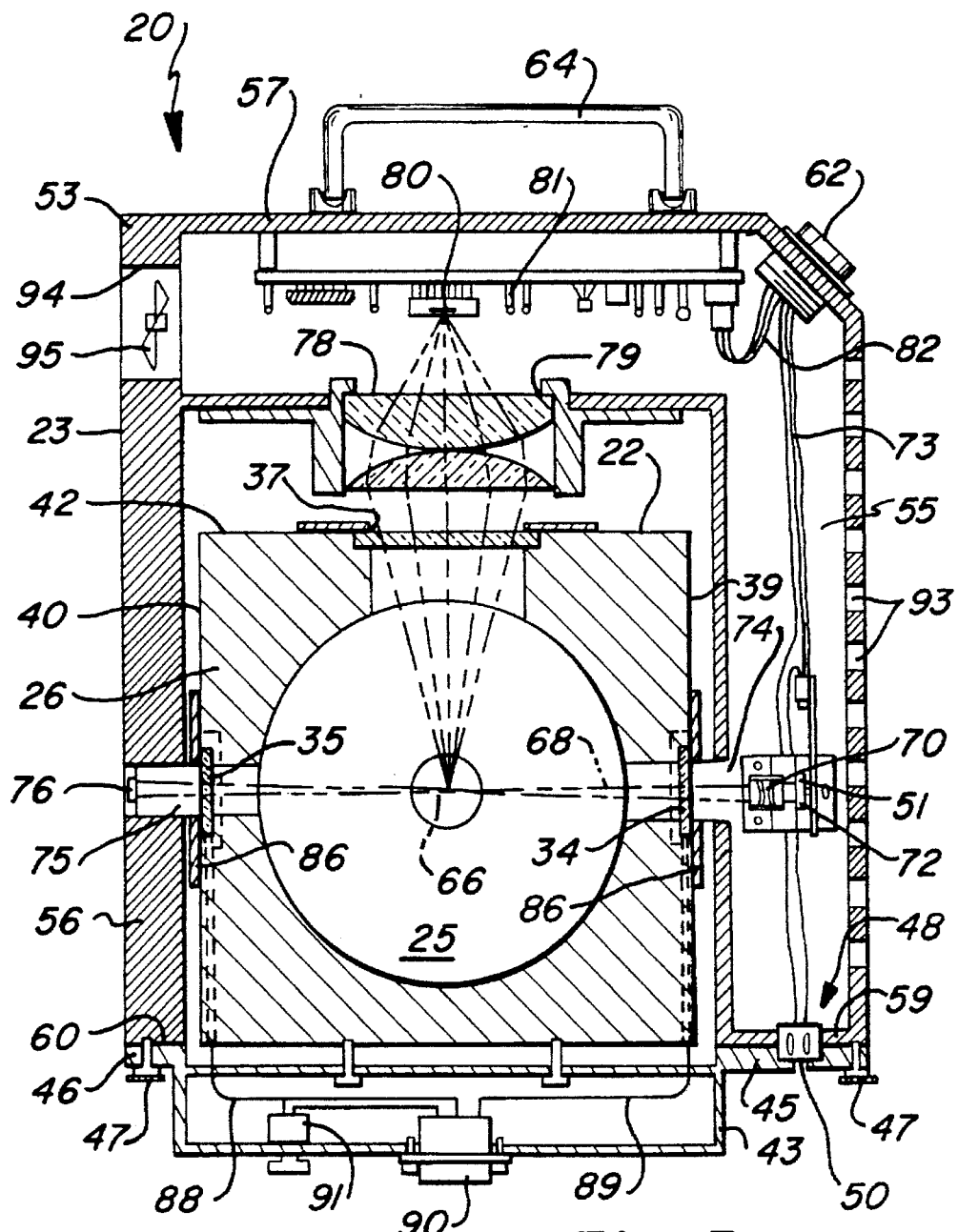
Fig_5
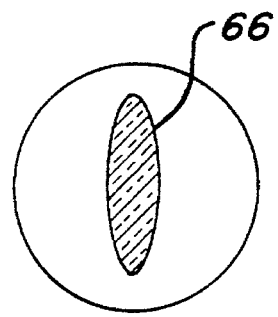
Fig_6

1

NONINTRUSIVE MODULAR PARTICLE DETECTING DEVICE

FIELD OF THE INVENTION

This invention relates to in-situ detection of particles in a fluid, and, more particularly, relates to a modular particle detecting device for nonintrusive detection of particles in a fluid.

BACKGROUND OF THE INVENTION

Detection and/or measurement of particles in a fluid is well-known, and such detection and/or measurement has heretofore been effected by a number of devices, including devices which illuminate a sample region to cause light to be scattered by particles in the fluid with the scattered light then being detected and processed to provide an indication and/or measurement of a parameter thereof, such as particle size.

In-situ measurement of particles in a fluid has been hertofore proposed and/or utilized for contamination control in connection with various process tools, including process tools used in semiconductor process environments.

Now known instruments using light scattering to size particles to thereby monitor contaminants are normally either intrusive type instruments wherein the sensing mechanism intrudes into the process environment (as is illustrated in FIG. 1 showing, typically, detectors 8 mounted on opposite walls of sensor unit 9 having laser beam 10 directed therethrough, with sensor unit 9 being inserted through aperture 11 into flow line 12), or are nonintrusive type instruments wherein the sensing mechanism is maintained outside the process environment (as is illustrated in FIG. 2 showing, typically, detection of light scattered by particles at sample region 14 within flow line 15 using reflector 16 to direct scattered light to detector 17 connected with processing circuitry 18 with reflector 16, detector 17 and processing circuitry 18 all being mounted outside of flow line 15).

Intrusive and nonintrusive type instruments, have been heretofore used, or suggested for use, under differing conditions, and either type of unit can, for example, be used to view a sample area, or region, in a process exhaust line (ie, pumpdown line). Intrusion type instruments, have, however, proved to be undesirable for at least some flow line uses due to necessary physical intrusion of this type of instrument into the flow line (in the case of an exhaust line, for example, the conductance of the exhaust line is reduced thereby changing the pumpdown characteristics for the process tool).

Both intrusive and nonintrusive type instruments, now known, have exhibited characteristics which can severely limit both performance and reliability of such instruments. In some cases, such instruments have been rendered ineffective in some process environments, particularly where such process environment has a contaminating or corrosive nature. Optical and electrooptical components that are exposed to such an environment can, for example, have contamination problems due to corrosion and/or deposition of/by materials from the process tool. This results in degradation of instrument performance and/or instrument failure depending on the severity of the contamination.

While purged gas has heretofore been used upstream from detecting instruments in an attempt to help shield such instruments from contamination, such purging often has failed to satisfactorily solve the problem and can, at least in some cases, adversely affect process operating parameters.

Now known instruments have also been singular instruments with a viewing section and a detecting section in the same housing. The singular nature of such instruments has resulted in imposition of undesirable restraints in use as well as precluding at least some types of improvements to the instruments, including, for example, heating of optics (since such heating would also undesirably heat other components, such as laser sources, detectors and associated electronics, often resulting in dramatically increased failure rates for such components) and/or easy instrument servicing or verification (since removal of the instrument requires a break in the associated flow line and hence requires process tool shutdown when the flow line break disrupts operation of the process tool as, for example, where the flow line break results in a break in vacuum).

SUMMARY OF THE INVENTION

This invention provides an improved in-situ particle measuring device that is physically nonintrusive to minimize the adverse effects of harsh process environments on performance and reliability, and is modular to allow both device improvement and ready servicing or verification.

By providing a viewing unit that is separate from the sensing unit, optics at the viewing unit can be heated without undesirable heating of the components of the sensing unit to thereby reduce the amount of contamination, through elimination of condensation at the viewing unit. In addition, since only the viewing unit is connected with an associated flow line, the sensing unit can be removed from an operational position adjacent to the viewing unit without requiring that the flow of fluid through the flow line be interupted, and hence the sensing unit can be readily removed for servicing or verification, and can, if needed or desired, be utilized at additional areas in conjunction with a different viewing unit.

It is therefore an object of this invention to provide an improved particle detecting and/or measuring device.

It is another object of this invention to provide an improved in-situ particle detecting and/or measuring device that is nonintrusive.

It is still another object of this invention to provide an improved particle detecting device that is modular.

It is still another object of this invention to provide a modular particle detecting device having separate viewing and sensing units.

It is still another object of this invention to provide a modular particle detecting device having a viewing unit with heatable windows whereby contamination is reduced by eliminating condensation at said windows.

It is still another object of this invention to provide a modular particle detecting device allowing removal of a sensing unit without removal of an operationally associated viewing unit thereby allowing continued operation of a system having the viewing unit connected therewith.

It is still another object of this invention to provide a modular particle detecting device allowing removal of a sensing unit from a viewing unit for servicing, verification and/or alternate use of the removed sensing unit.

It is yet another object of this invention to provide a sensing unit that is usable with a separate viewing unit.

With these and other objects in view, which shall become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical of the principles thereof, and in which:

FIG. 1 is a partial side view illustrating typically, as prior art, an intrusive type instrument for detecting particles in a flow line;

FIG. 2 is a partial side view illustrating typically, as prior art, a nonintrusive type instrument for detecting particles in a flow line;

FIG. 3 is an exploded perspective view of the modular particle detecting device of this invention;

FIG. 4 is a partial perspective view illustrating the viewing unit of the modular particle detecting device of this invention, as show in FIG. 3, connected to a flow line;

FIG. 5 is a top section view of the assembled modular particle measuring device of this invention as shown in FIG. 3, but rotated with respect thereto; and FIG. 6 is a section view illustrating, in greater detail, the sensing region, as indicated in FIG. 5.

DESCRIPTION OF THE INVENTION

Modular particle measuring device 20, as best shown in FIG. 3, includes viewing unit 22 and sensing unit 23. Viewing unit 22 has a central bore, or passage, 25 extending through viewing element or block 26, and viewing block 26 terminates at flanges 28 and 29 at opposite ends of passage 25 to fascillitate connection of viewing block 26 to flow line 31 by means of clamp 32 (as shown in FIG. 4).

Illuminating window 34, discharge window 35, and detecting, or viewing, window 37 are centrally mounted at sides 39, 40 and 42 of rectangularly shaped viewing block 26 (illuminating window 34 and discharge window 35 are aligned with and are at opposite sides 39 and 40 of the viewing block, as best shown in FIG. 5). As shown in FIGS. 3 and 5, mounting bracket 43 is connected to the central portion of viewing block 26 (which may be of stainless steel and, as shown in FIG. 3, may be a cube), and mounting bracket 43 includes mounting walls 45 and 46 extending outwardly in opposite directions from the viewing block to enable mounting of sensing unit 23 on viewing unit 22, as by means of screws 47 as indicated in FIGS. 3 and 5. As also indicated, a laser interlock 48 that includes a plug 49 at wall 45 of sensing unit 22 and a connector 50 at sensing unit 23 to assure shutdown of laser 51 whenever the sensing unit is removed from the viewing unit.

Sensing unit 23 includes generally U-shaped housing 53 (which may be of aluminum) having leg portions 55 and 56 and bridging portion 57 extending between the leg portions. End portions 59 and 60 of leg portions 55 and 56, respectively, are engagable with walls 45 and 46, respectively, of viewing unit 22 when the viewing unit and the sensing unit are connected for operation of the device in detecting particles, as brought out more fully hereinafter. Electrical connector 62 is provided at the junction of leg portion 55 and bridging portion 57, and since sensing unit 23 is portable when removed from viewing unit 22, bridging portion 57 may have a convenient carrying handle 64 thereon.

FIG. 5 illustrates sensing unit 23 asembled, or operatively connected, to viewing unit 22. As shown, sensing, or sample, region 66 is within passage 25, and the sensing region is illuminated by directing laser beam 68 from condensor 70, connected with laser diode 72 (both of which are located in leg 55 of viewing unit 23 and with laser diode 72 being connected with a power source through electrical leads 73 one of which leads extends to and from connector 50 of laser interlock 48 to break the power connection to the laser diode whenever the sensing unit is not operatively positioned at the viewing unit) through aperture 74 in leg 55 of housing 53 and then through illuminating window 34 of the viewing unit so that the laser beam passes through the sensing region. The portion of the light provided by the laser beam not scattered by particles at sensing region 66 then passes from the viewing unit through discharge window 35 (aligned with illuminating window 34) and aperture 75 in leg 56 of housing 53 to a light absorbing beam stop (or block) 76 located in leg 56 of the viewing unit. As also shown in FIG. 5, light scattered by particles at sensing region 66 passes through detecting window 37 and is collected by imaging system 78 (having collecting optics) positioned at aperture 79 of bridging portion 57 of housing 53, with the collected light from the imaging system being focused onto a detector unit 80 (such as a photodetector and, preferably an array of photodetectors) of detecting circuitry 81 positioned within bridging portion 57 of housing 53.

A 40 mm$^2$ sample area 66 is preferably optically defined by using a ½ magnification imaging system 78, a 2 mm depth of field, a 10 mm long photodetector unit 80, and, as indicated in FIG. 6, a 100 um×2 mm beam cross-section in the center of the viewing module (1/(½)×10 mm×2 mm=40 mm$^2$).

Light scattered at a 90° angle by particles passing through the sensing region is collected and focused onto the photodector unit where the light photons are converted to electrons. The resulting electrical signal is coupled from the sensing unit through electrical leads 82 to remotely situated circuitry for conventional processing, including measurement of a preselected parameter such as, for example, particle sizing using pulse height analysis circuitry.

The remotely situated circuitry normally includes, for example, power supplies, signal conditioning electronics, and a microprocessor for processing of data, as well as the before-mentioned pulse height analysis circuitry. Particle measurement could also be carried out, for example, using processing circuitry as described in U.S. Pat. No. 4,798,465. Particle sizing techniques are also discussed in an article entitled "Optical Particle Monitors, Counters and Spectrometers: Performance Characterization, Comparison And Use", by Dr. Robert G. Knollenberg and Dr. Donald L. Veal, 37th Annual Technical Meeting , Inst. of Envir. Sci., May 1991.

If needed, or desired, the electrical signal developed at detecting unit 80 could also be partially processed (or in some cases entirely processed), including amplifying the signal, in housing 53 prior to coupling the signal from the sensing unit.

By use of viewing unit 23 separate from sensing unit 22, the windows of the sensing unit (and particularly the illuminating and discharge windows) can be heated. This is accomplished by plug heaters 86 located so that the temperature of illuminating window 34 and discharge window 35 is maintained at approximately 150° C. Power is supplied to electric heaters 86 through electrical leads 88 and 89 connected with power supply plug 90 (having circuit breaker 91 connected therewith) with plug 90 being connectable with a conventional 115 volt power source.

Viewing unit, or module, 22 is thermally isolated from sensing unit 23 through the use of spacers and air gaps so that the temperature inside housing 53 never exceeds about 50° C. This temperature limit is further assured through introduction of outside cooling air into the housing with the outside cooling air being introduced into housing 53 through inlets, or vents, 93 in leg 55 and exhausted at outlet 94 in leg 56 using fan 95.

The sensing unit can be removed from the viewing unit without breaking a flow line having the viewing unit therein (and thus without breaking the vacuum inside the flow line where the process is a vacuum process). This allows servicing of the sensing unit without interrupting the operation of the process tool. It also allows the sensing unit to be used with a different viewing unit located at different sites.

The nonintrusive modular particle detecting device of this invention has been used to detect submicron size particles in a fluid, such as gases or wet chemicals, with detection of particles smaller than 0.2 microns having been achieved.

As can be appreciated from the foregoing, the modular particle detecting device of this invention is improved in operation and the sensing unit can be readily removed from the viewing unit to allow servicing, verification and/or alternate use without disrupting fluid flow through a flow line connected with the viewing unit.

What is claimed is:

1. A nonintrusive particle detecting device, comprising:

a viewing unit having first wall means defining a fluid passage, said viewing unit being connectable to a flow line passing fluid having particles therein so that said fluid passes through said fluid passage, said first wall means having window means therein, and said viewing unit having second wall means connected with and extending outwardly from said first wall means; and a sensing unit having housing means engaging said second wall means of said viewing unit to position said sensing unit in operating position adjacent to said viewing unit with said housing means being removable from said engagement with said second wall means of said viewing unit to thereby remove said sensing unit from said operating position without requiring interference with fluid flow through said fluid passage of said viewing unit, said sensing unit also having illuminating means for providing light through said window means to a predetermined sensing region in said fluid passage whereby particles in fluid then at said sensing region cause said light to be scattered, and said sensing unit also having detecting means for receiving, through said window means, light scattered by particles at said sensing region and, responsive thereto, providing an output indicative of said particles.

2. The device of claim 1 wherein said viewing unit is connected with said flow line by releasable fastening means.

3. The device of claim 1 wherein said flow line is a process exhaust line, and wherein said device is utilized for control of contamination indicated by particles detected in said fluid passage.

4. The device of claim 1 wherein said window means includes a first window through which light is provided to said sensing region and a second window through which scattered light is provided to said detecting means.

5. The device of claim 1 wherein said viewing unit includes heating means for heating said window means.

6. The device of claim 1 wherein said second wall means of said viewing unit includes first and second mounting flanges extending outwardly in opposite directions from said first wall means, and wherein said housing means of said sensing unit includes end portions engaging said first and second mounting flanges when said sensing unit is in operating position, said housing means having said illuminating means and said detecting means therein.

7. The device of claim 6 wherein said sensing unit includes cooling means for cooling said illuminating means and said detecting means within said housing means.

8. The device of claim 1 wherein said illuminating means is a laser diode, and wherein said sensing means includes optic means for receiving light scattered at said sensing region and directing said received scattered light to said detecting means.

9. The device of claim 8 wherein said device includes laser interlock means at said second wall means for terminating operation of said laser diode upon removal of said sensing unit from said operating position adjacent to said viewing unit.

\* \* \* \* \*